(12) United States Patent
Streit et al.

(10) Patent No.: US 12,403,241 B2
(45) Date of Patent: Sep. 2, 2025

(54) MODULAR ADMINISTRATION APPLIANCE

(71) Applicant: TecMed AG, Burgdorf (CH)

(72) Inventors: Ursina Streit, Kirchberg (CH); Thomas Buri, Burgdorf (CH); Christophe Hofer, Burgdorf (CH); Patrick Hostettler, Hasle (CH); Bernhard Bigler, Niederönz (CH); Simon Martin Bosshard, Bern (CH); Jürg Steck, Kirchberg (CH); Thomas Leuzinger, Münsingen (CH); Clemens Zürcher, Ranflüh (CH)

(73) Assignee: TecMed AG, Burgdorf (CH)

( * ) Notice: Subject to any disclaimer, the term of this patent is extended or adjusted under 35 U.S.C. 154(b) by 911 days.

(21) Appl. No.: 17/374,213

(22) Filed: Jul. 13, 2021

(65) Prior Publication Data

US 2021/0338924 A1    Nov. 4, 2021

Related U.S. Application Data

(63) Continuation of application No. PCT/IB2019/059913, filed on Nov. 19, 2019.

(30) Foreign Application Priority Data

Jan. 17, 2019   (CH) .................................. 00055/19

(51) Int. Cl.
*A61M 5/14*    (2006.01)
*A61M 5/142*   (2006.01)
*A61M 5/145*   (2006.01)

(52) U.S. Cl.
CPC ...... *A61M 5/1413* (2013.01); *A61M 5/14248* (2013.01); *A61M 5/14566* (2013.01);
(Continued)

(58) Field of Classification Search
CPC ...... A61M 5/1413; A61M 2005/14268; A61M 2005/14573; A61M 5/14566; A61M 5/14248
See application file for complete search history.

(56) References Cited

U.S. PATENT DOCUMENTS 5,941,846 A *  8/1999  Duffy ................... A61M 5/172
                                                  604/65
6,585,695 B1   7/2003  Adair et al.
(Continued)

FOREIGN PATENT DOCUMENTS

CH         715757 A2    7/2020
CN      102083483 A    6/2011
(Continued)

OTHER PUBLICATIONS

Search Report issued in Chinese Patent Application No. 201980089409. 6, mailed on Oct. 10, 2022, 3 pages.
(Continued)

*Primary Examiner* — Courtney B Fredrickson
*Assistant Examiner* — Kayla M. Turkowski
(74) *Attorney, Agent, or Firm* — Dorsey & Whitney LLP

(57) ABSTRACT

A modular device for administering a fluid medicament fixable to the skin of a user includes a reservoir module with a reservoir defining a first axis, a first connecting structure and a first electrical contact arrangement; and a pump module with a piston rod defining a second axis, a second connecting structure arranged around the piston rod, and a second electrical contact arrangement. The first and second connecting structures are plugged together and the first axis and the second axes lie on a common axis forming a rotational axis. The pump module is rotated relative to the reservoir module about this rotational axis to electrically connect the first and second electrical contact arrangements. The first contact arrangement is displaced radially farther (Continued)

from the first axis than the first connecting structure, and the second electrical contact arrangement is displaced radially farther from the second axis than the second connecting structure.

16 Claims, 6 Drawing Sheets

(52) U.S. Cl.
CPC ............ *A61M 2005/14252* (2013.01); *A61M 2005/14268* (2013.01); *A61M 2205/123* (2013.01); *A61M 2205/8206* (2013.01)

(56) References Cited

U.S. PATENT DOCUMENTS

| | | | |
|---|---|---|---|
| 2004/0064096 A1 | 4/2004 | Flaherty et al. | |
| 2011/0160652 A1 | 6/2011 | Yodfat et al. | |
| 2015/0025503 A1 | 1/2015 | Searle et al. | |
| 2016/0339170 A1* | 11/2016 | Shapley | A61M 5/50 |
| 2016/0339172 A1 | 11/2016 | Michaud et al. | |
| 2016/0339174 A1 | 11/2016 | Shapley et al. | |
| 2016/0361494 A1* | 12/2016 | Jürg | A61M 5/14244 |
| 2017/0215702 A1* | 8/2017 | Niwa | G02B 23/2476 |
| 2018/0264189 A1 | 9/2018 | Michaud et al. | |
| 2018/0264192 A1 | 9/2018 | Yodfat et al. | |
| 2020/0086044 A1* | 3/2020 | Streit | A61M 5/14248 |

FOREIGN PATENT DOCUMENTS

| | | |
|---|---|---|
| CN | 102186515 A | 9/2011 |
| CN | 103228303 A | 7/2013 |
| CN | 106029125 A | 10/2016 |
| CN | 108472441 A | 8/2018 |
| EP | 3501569 A1 | 6/2019 |
| EP | 3501573 A1 | 6/2019 |
| EP | 3501577 A1 | 6/2019 |
| EP | 3636298 A1 | 4/2020 |
| WO | 2009125398 A2 | 10/2009 |
| WO | 2010022069 A2 | 2/2010 |
| WO | 2012040528 A1 | 3/2012 |
| WO | 2015127965 A1 | 9/2015 |
| WO | 2017118540 A1 | 7/2017 |
| WO | 2018229783 A1 | 12/2018 |
| WO | 2020148581 A1 | 7/2020 |

OTHER PUBLICATIONS

International Preliminary Report on Patentability issued in International Application No. PCT/IB2019/059913, mail on Jun. 16, 2021, 8 pages.

English translation of International Search Report issued in International Application No. PCT/IB2019/059913, mailed on Feb. 6, 2020, 2 pages.

* cited by examiner

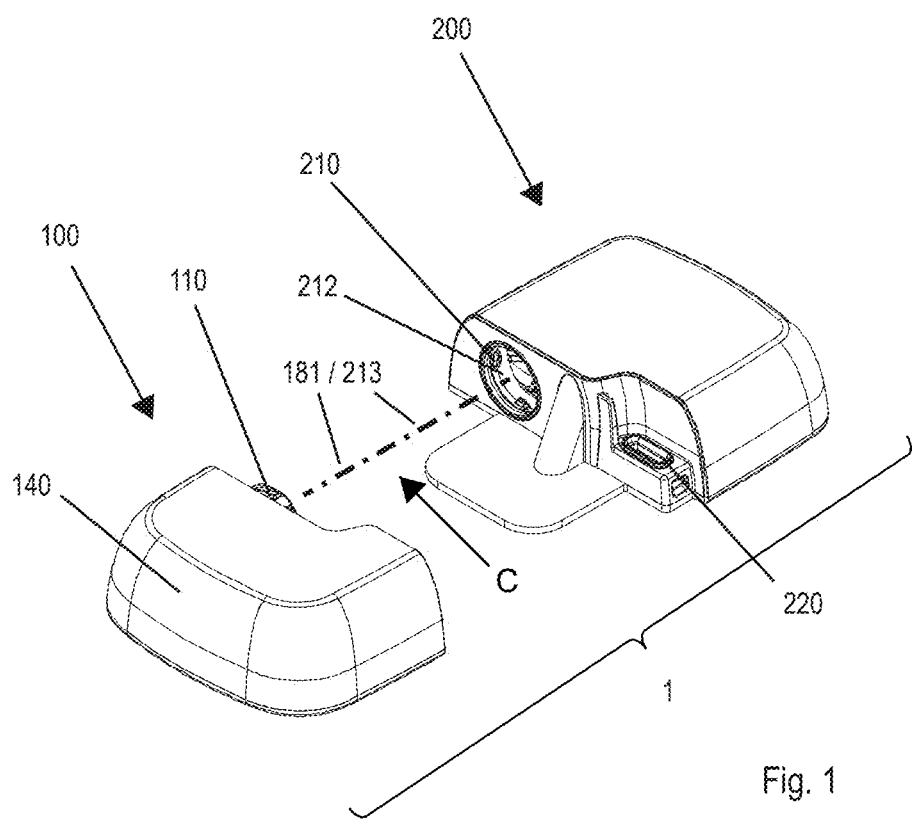

MODULAR ADMINISTRATION APPLIANCE

CROSS-REFERENCE TO RELATED APPLICATIONS

This application claims priority to International Patent Application No. PCT/IB2019/059913, filed Nov. 19, 2019, entitled "IMPROVED MODULAR ADMINISTRATION APPLIANCE," which in turn claims priority to Swiss Patent Application No. CH 00055/19, filed Jan. 17, 2019, entitled "IMPROVED MODULAR ADMINISTRATION APPLIANCE", each of which is incorporated by reference herein, in their entirety and for all purposes.

TECHNICAL FIELD

Implementations are directed to the field of administration appliances, such as wearable infusion pumps, including infusion pumps that can be worn on and affixed to the skin of users, such as for the administration of insulin.

BACKGROUND

Administration appliances that can be used to administer fluid medicament formulations are known from the prior art. An administration device for administration of insulin that can be affixed directly on the skin of the user is known from US20040064096 A1. It is a so-called Pflasterpumpe or patch pump, where the term "Patch Pumpe" is also used in German. Said patch pumps have the advantages that they can be worn discretely under clothing, can be made very compact, can be operated wirelessly via a remote radio control, and for the most part do not require a separate infusion kit. In the case of US20040064096 A1, it is disadvantageous that after the reservoir has been emptied the entire pump must be discarded, including all potentially reusable parts.

A patch pump that has a modular construction is known from US2011160652 A1; the modular patch pump consists of a base plate, which is adhered to the skin of the user and via which a cannula, through which a medicament can be administered, penetrates into tissue. The patch pump further comprises a reservoir module, which is designed as a single-use module, and a reusable pump module. Here the pump module contains, among other things, the control electronics and the electrical drive. For use, the reservoir module and pump module are plugged and connected together. The reservoir module contains an energy source, which can provide the electronics and the drive with power when the two modules are plugged together. For this, the reservoir module and the pump module have electrical contacts, which are connected to each other when the modules are connected together and thus enable the supply of energy to the pump module. Because of the simple plug connection between reservoir module and pump module, it is, in the case of the device described in US2011160652 A1, difficult to make a clean and reproducible electrical contact between reservoir module and pump module. For example, the pump module, which must be replaced regularly (typically every three days) and is made in large numbers, is subject to geometric production tolerances that can adversely affect the electrical contact. In each case according to the selected allocation of the drive parts between pump module and reservoir module, it can be that the plug connection must be able to accommodate the drive forces, which makes the design of the plug connection more challenging or limits the possibility for allocation of parts between pump module and reservoir module. Thus, it appears not to be without good reason that in US2011160652 A1 the piston rod is disposed in the reservoir module and only a rotary motion is transmitted from the pump module to the piston rod.

Therefore, there is a need for an administration device in which said problems are addressed.

In this connection, the terms "medicament," "fluid medicament formulation," or "medicinal substance" comprise any flowable medicinal formulation that is suitable for controlled administration via a cannula or hollow needle, for example a liquid, a solution, a gel, or a fine suspension containing one or more medicinal agents. A medicament can therefore be a composition containing a single active agent or a premixed or co-formulated composition with a plurality of active agents from a single container. The term in particular comprises drugs like peptides (for example insulins, insulin-containing medicaments, GLP-1-containing preparations as well as derived or analogous preparations), proteins and hormones, biologically obtained or active agents, active agents based on hormones or genes, nutrient formulations, enzymes and other substances, both in solid (suspended) or liquid form. The term further also comprises polysaccharides, vaccines, DNA or RNA (including mRNA), or oligonucleotides, antibodies or parts of antibodies, as well as suitable basis substances, adjuvants, and vehicles.

The term "distal" refers to a direction toward the puncturing side or end of the administration device. In contrast, the term "proximal" refers to a direction toward the rear side or end, opposite the puncturing side or end of the administration device.

SUMMARY

Implementations of the present disclosure provide a modular administration device with an improved electrical contact between modules of the administration device.

In a first implementation, an administration device is configured as a patch pump. The patch pump is provided in modular form and includes a reservoir module and a pump module. The reservoir module includes a housing and a fillable reservoir in the shape and configuration of a cartridge, which by its cylindrical shape defines a first axis, where a cross section of the reservoir may be round, oval, or even rectangular, and the walls of the reservoir may be rigid or deformable. A slidable stopper or piston may be disposed in the reservoir, where the volume within the reservoir may be varied, for instance reduced, by a sliding of the stopper or piston. The proximal end of the reservoir may be open and accessible through an opening in the housing of the reservoir module, through which the stopper or piston may also be made accessible. Furthermore, the reservoir module may include a first connecting structure to connect the reservoir module and pump module, as provided herein. The connecting structure may be arranged around the housing opening on the housing of the reservoir module. The reservoir may further include a first electrical contact arrangement for electrical contact with the pump module and may be arranged on the housing of the reservoir module. In implementations, the reservoir module may further include an energy source, such as a battery or primary energy source, to supply the administration device with electrical energy.

The reservoir may be configured as an elongated pouch, and instead of a stopper or piston, at least one movable pressure or squeeze element may be provided to compress the pouch in order to reduce the reservoir volume.

The pump module may include a housing and a piston rod, which may be positioned movably and at least partially in the housing of the pump module. The housing of the pump module may include an opening through which the piston rod can be moved. The piston rod may define a second axis. A second connecting structure may be arranged around the opening in the pump module housing and may be configured for connecting to the reservoir module, as provided herein. The pump module may further include a second electrical contact arrangement for electrical contact with the reservoir module and may be disposed on or in the housing of the pump module. In embodiments, the pump module may further include a secondary energy source and/or energy store, in such as a rechargeable battery or a capacitor, which may be charged, to store and release electrical energy.

The reservoir module and pump module may be connected together via a plug-and-rotation connector, such as a bayonet connector, as known to those skilled in the art. In this case, the first connecting structure may be the first part of the bayonet connector and the second connecting structure may be the second part of the bayonet connector. To assemble the bayonet connector, the pump module and the reservoir module may be aligned so that the openings are across from each other and the first and the second axes coincide, thus forming a common axis, e.g., a common axis of rotation for connection. Then the two modules may be pushed together, where care should be taken to ensure that the modules are rotationally aligned so that the connecting structures allow such pushing together. After the modules have been pushed together, the connection may be securely completed by relative rotation of the modules. Upon rotation, on the one hand, the modules may be slightly drawn towards each other, so that any production tolerances (and/or play between the parts) may be compensated for, and on the other hand, at the end of the rotation a separable or releasable locking takes place, so that the two modules may no longer be moved relative to one another upon being locked together. After the two modules have been locked together, the piston rod may be moved into the reservoir, such that the stopper or piston may be moved in the distal direction by the piston rod in order to force the medicament formulation from the reservoir.

The electrical contact (electrically conducting contact) between the first electrical contact arrangement and the second electrical contact arrangement may also be established during the rotation of reservoir module and pump module relative to each other upon assembling the bayonet connector. In this case a sequence in which the respective electrical contacts of the contact arrangements or structures come into contact can be specified; thus, it may be advantageous if a grounding contact between the modules is made first. In one example according to implementations of the present disclosure, the first electrical contact arrangement may be disposed on the same housing side as the opening in the reservoir module and the second electrical contact arrangement may be disposed on the same housing side as the opening in the pump module.

According to implementations of the present disclosure, the first and the second electrical contact arrangements may have a separation or displacement from the first or second axes (after the pushing together of and the formation of a common axis of rotation) that is greater than that of the first or second connecting structure from the relevant axis. This has the advantage that the arcuate or rotational path of the first and second electrical contact arrangement described in the assembly of the bayonet connection (rotation) can be longer relative to each other than the arcuate or rotational path of the first and second connecting structures to each other. As a result, a motion, translation or transfer along the path may enable a secure and low resistance contact in the making of the electrical contact between the modules. The arrangement of the first and second electrical contact arrangements according to the present disclosure differs from those bayonet connector solutions in which the electrical contact arrangements come to lie on the connecting structures themselves, for example on the axial connecting structures, or relatively closer to the axes, since there the possible motion path for making a clean electrical contact is considerably shorter.

In one implementation of the present disclosure, the first electrical contact arrangement may include at least one socket, where each socket may be used, for example, for one contact in the electrical contact arrangement. In a complementary fashion, the second electrical contact arrangement in one implementation of the present disclosure includes at least one pin, such as at least one spring pin or elastic pin. Upon assembly of the bayonet connection, as the two modules are rotated opposite to one another, the at least one pin defines the path of an arc segment as it becomes plugged into the at least one socket. One should note here that the at least one pin may be disposed tangentially to the arc. An advantage according to the present disclosure may be provided through the motion, translation or transfer along the arc or rotational path, since the pin(s) and socket(s) may thus be displaced from the actual bayonet connector.

In one implementation of the present disclosure, the first electrical contact arrangement may be configured as a post socket and the second electrical contact arrangement as a post plug or pin(s), or vice versa. The sockets or pins or plugs (i.e., their axes) may be generally or approximately perpendicular to the first axis or the second axis, respectively.

In some configurations, the first electrical contact arrangement may include four post sockets, which, for example, may be combined into a single-row or multi-row post socket; complementary to the second electrical contact arrangement, which may include four contact posts or pins, and which may be combined into a post or pin plug. In this case, two contacts may serve for energy supply, in which electrical energy may be transmitted from the reservoir module to the pump module. The other two contacts may be used for signal transmission, such as to transmit information from the reservoir module to the pump module and to transmit control signals from the pump module to the reservoir module. In some configurations, however, more or fewer contacts may be provided for signal transmission and transmission may be bidirectional.

In another configuration, the first electrical contact arrangement may be configured as a single socket with a plurality of contacts and correspondingly the second electrical contact arrangement may be configured as a single plug with a plurality of contacts. This may be analogous to connection types such as USB, Lightning, headset, or earphone jacks.

In one implementation of the present disclosure, the first electrical contact arrangement may be floating on or in the reservoir module. The term "floating" means that the first electrical contact arrangement has a certain ability to move relative to the housing of the reservoir module. In this case, a movability such as (but not, however, necessarily only) transverse to the assembling motion during connection rotation may be provided. This movability may enable compensation of manufacturing tolerances on the reservoir module. The mobility may lie in the range of 1 to 3 mm, but may also be smaller, for example 0.4-0.8 mm. In a further design, the second electrical contact arrangement may be disposed rigidly on or in the pump module, in a complementary fashion to the "floating" first electrical contact arrangement. In this way, in the case of a pump module that is used over a long period of time with many reservoir modules, a stable and permanent arrangement may be selected while a flexible arrangement may be selected in the case of the first electrical contact arrangement, since it may need to participate in only a few assembling and separating operations of the bayonet connector.

In another implementation, the reservoir module may further include a fluid pathway, which may lead from the distal end of the reservoir to an infusion cannula, where the infusion cannula may be inserted into the tissue of a user, so that as the medicament formulation is displaced from the reservoir, the medicament formulation may travel from the reservoir through the fluid pathway into the tissue. In a further implementation, the reservoir module may additionally include an insertion device, with which the infusion cannula may be introduced into the tissue. In this regard, reference is made to the European patent application numbers 18199475.7, 17209749.5, 17209764.4, and 17209772.7, which are hereby incorporated by reference in their entirety into this patent application.

The connecting structures and electrical contact arrangements according to the present disclosure may include sealing elements, which may protect the reservoir module and/or pump module from undesirable entries of liquids. For example, the electrical contact arrangement on the reservoir module may comprise a sealing lip, which geometrically encircles the contacts in the electrical contact arrangement. When the modules are connected, the sealing lip may be compressed between the pump module and reservoir module and may thus seal the connection of the electrical contact arrangements. The sealing lip may be constructed with or include a plastic material, such as an elastomer plastic. Alternatively, the sealing lip may include an elastically or plastically deformable plastic, which may seal the gap between the electrical contact arrangements such as by plastic flow when the modules are connected, and the sealing lip may be disposed on the reservoir module in such configuration, since the sealing lip typically may be used only once. Analogously, sealing elements may be formed on the connecting structures.

A skin attachment patch of an administration device configured as a patch pump, according to the present disclosure, may be disposed on the housing of the reservoir module, such as firmly glued, bonded or welded. Alternatively, the patch may be disposed on a base plate that is separate from the reservoir and pump module, where in this case, the reservoir and pump module may be separately affixed to the base plate in the connected state, such as by being snapped on.

BRIEF DESCRIPTION OF THE DRAWINGS

Various implementations of the present disclosure are described herein in connection with the appended figures. These are intended to show the basic possibilities of the implementations herein and are not intended to be limiting in any way.

FIG. 1 illustrates a pump module and reservoir module of an administration device in a separated state, according to the present disclosure;

DETAILED DESCRIPTION

Figure 4A:
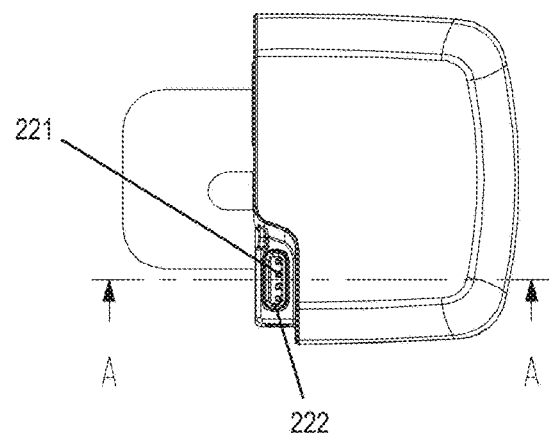
FIG. 4a illustrates a top view of the reservoir module of the administration device from FIGS. 3a and 3b.
Figure 4B:
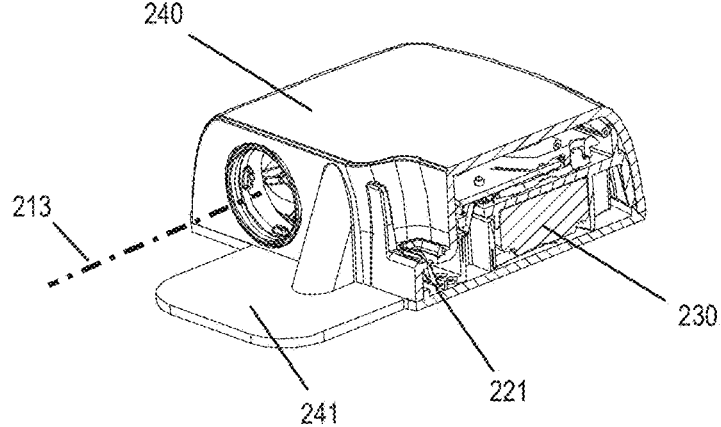
FIG. 4b illustrates a sectional view through line A-A of the reservoir module of the administration device of FIG. 4a, through the region of the electrical contact arrangements.
Figure 5A:
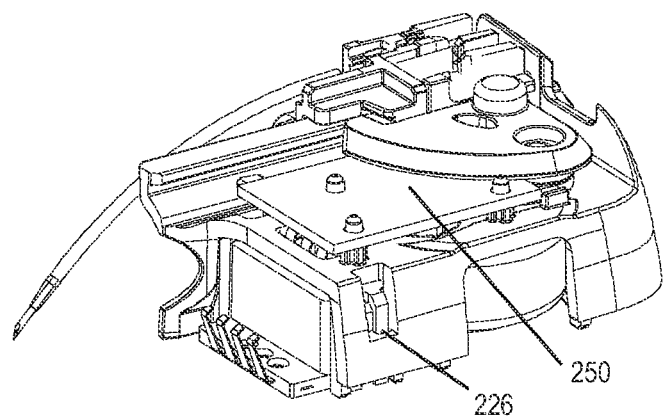
FIGS. 5a to 5c illustrate three detailed views of the reservoir module of FIG. 3b.
Figure 5B:
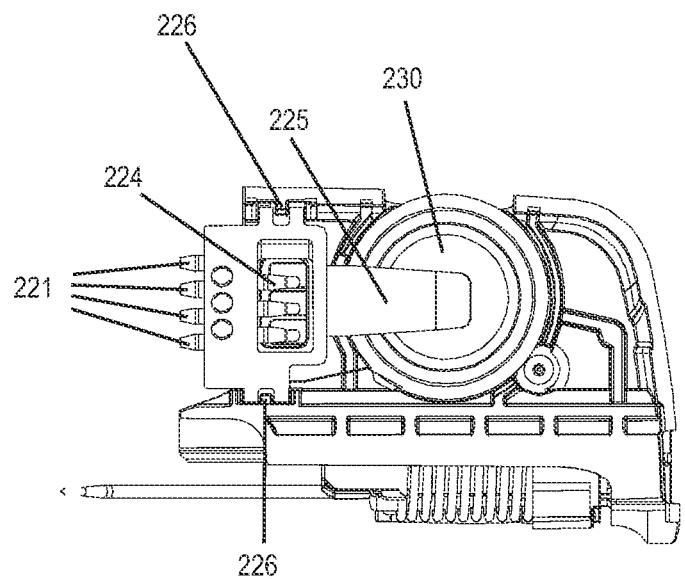
Figure 5C:
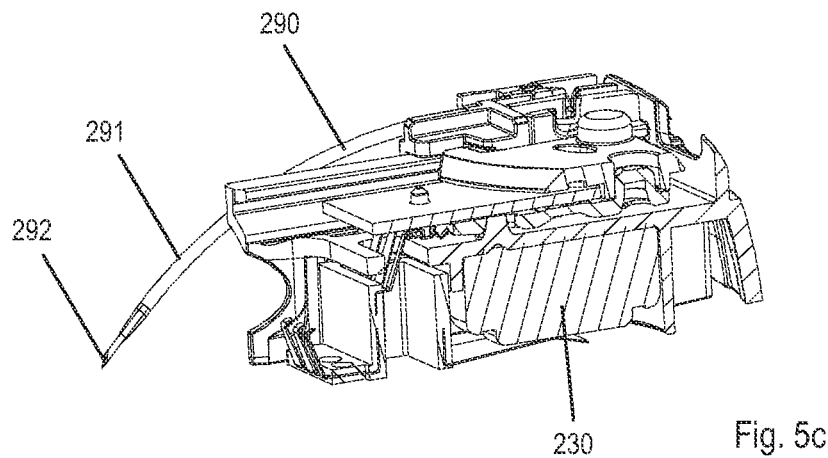
Figure 6:
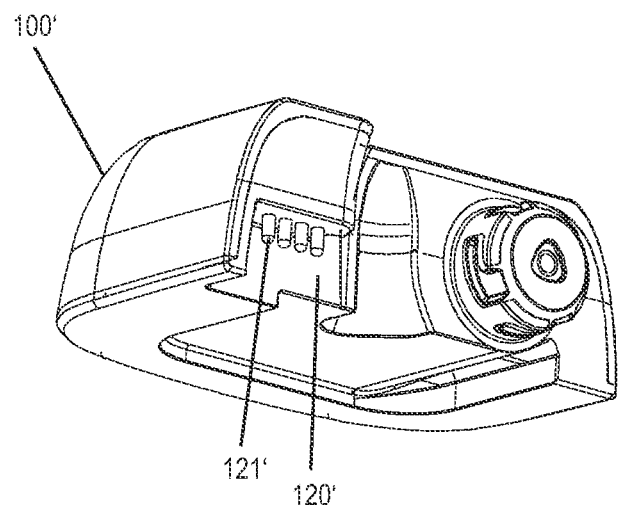
FIG. 6 illustrates an alternative implementation of the pump module having an electrical contact arrangement with pins.
Figure 7:
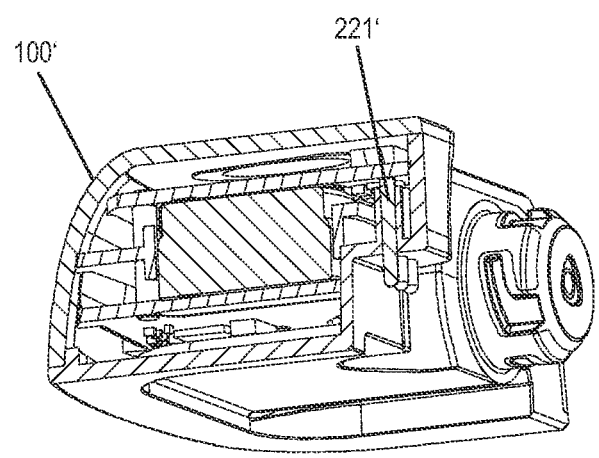
FIG. 7 illustrates a sectional view of an alternative implementation of the pump module in a sectional view having an electrical contact arrangement for connecting with sockets.
Figure 8A:
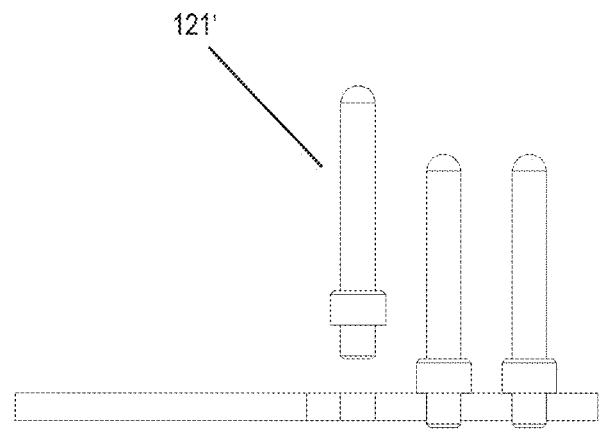
FIGS. 8a and 8b illustrate alternative configurations of the pin design for the electrical contact arrangements according to the present disclosure.
Figure 8B:
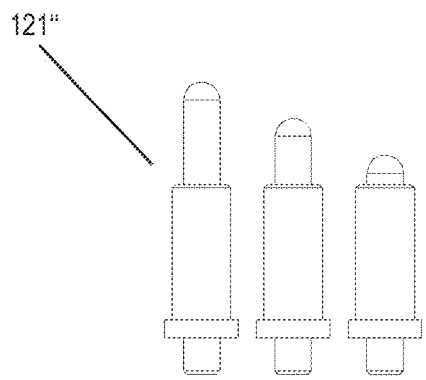

FIGS. 1-5c and FIG. 9 show a first implementation of the present disclosure. FIGS. 6 and 7 show a second implementation according to the present disclosure. FIGS. 8a and 8b show alternative pin designs of the second implementation.

Figure 2A:
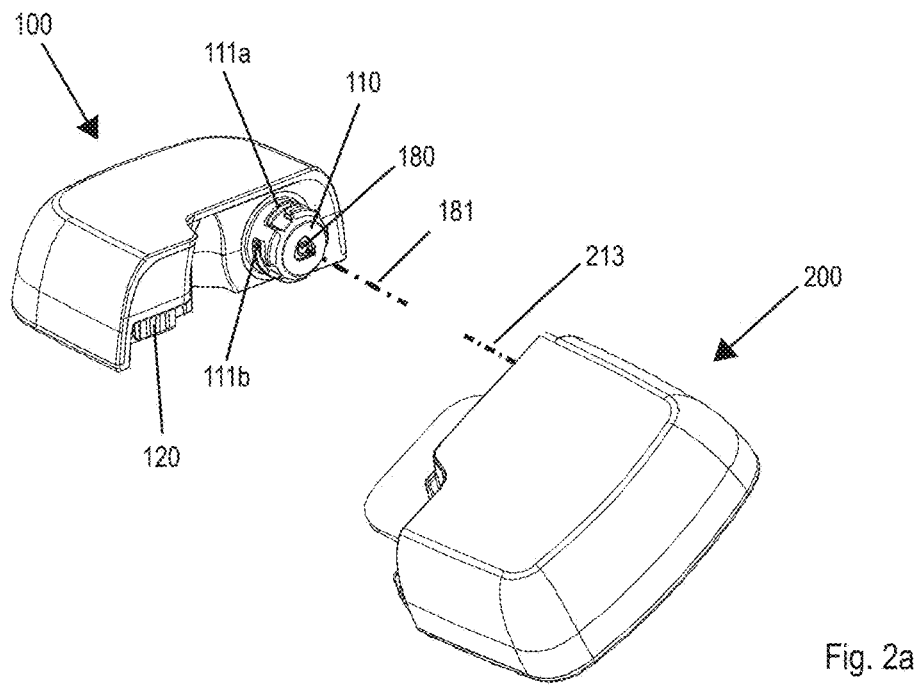
FIGS. 2a to 2c illustrate steps of the connection operation, in which the pump module and reservoir module are connected via a bayonet connector.
Figure 2B:
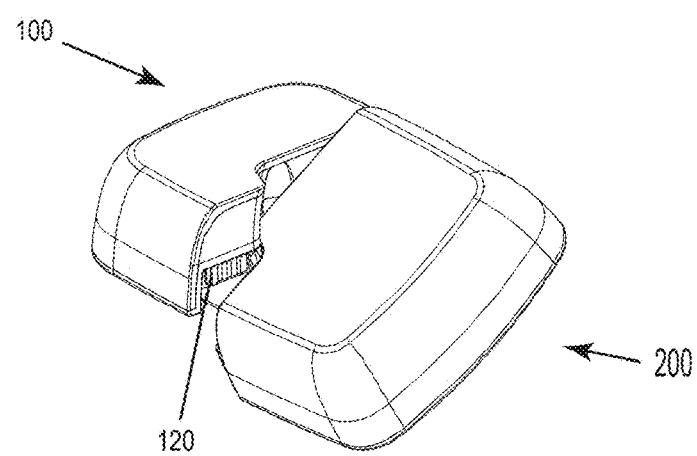
Figure 2C:
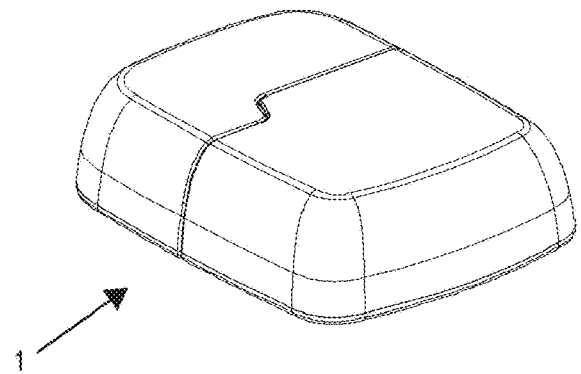
Figure 3A:
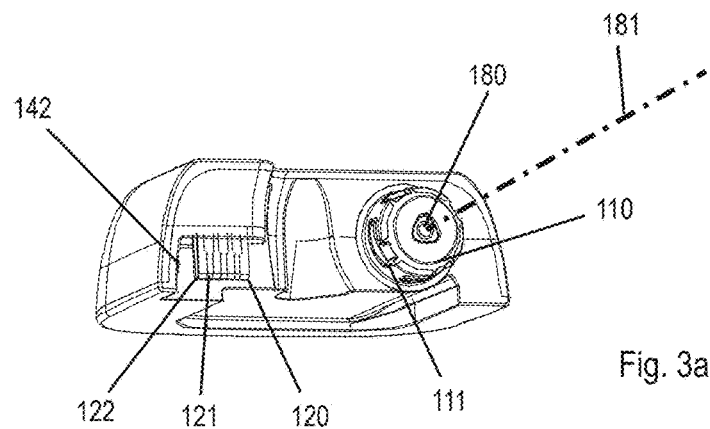
FIGS. 3a and 3b illustrate an embodiment of an administration device according to the present disclosure.
Figure 3B:
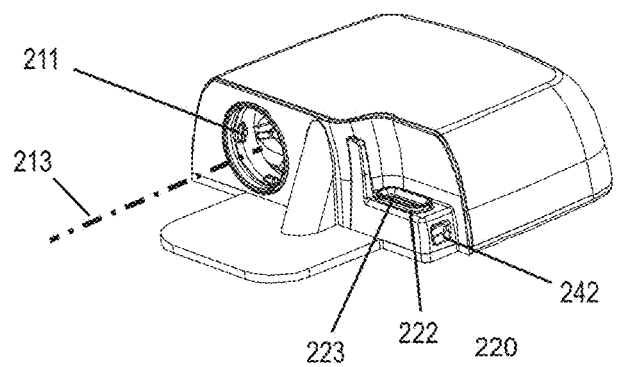
Figure 9:
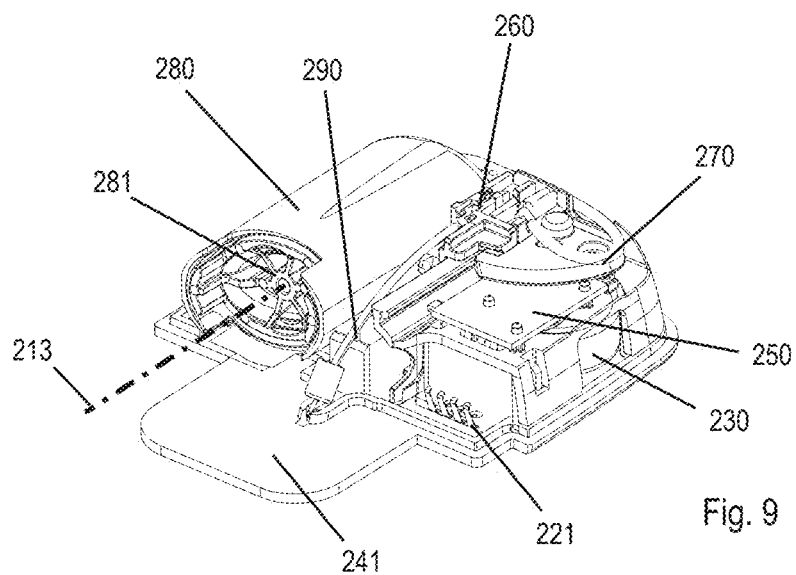
FIG. 9 illustrates the reservoir module of FIGS. 1-5c without the housing.

Reference will now be made to the first implementation, depicted in FIGS. 1 to 5 c and FIG. 9. The administration device 1 shown in FIG. 1 may be a modular patch pump (also called a plaster pump), which may be worn directly on the skin of the user. The administration device 1 may include the pump module 100 and the reservoir module 200. The pump module 100 in this case may be configured as a reusable module. The reservoir module 200 in this case may be configured as a single-use module (multi-use modules may also be possible without departing from the present disclosure). Pump module 100 and reservoir module 200 may be connected to each other via a bayonet connector. For this, the pump module 100 may include the connecting structure 110, which in turn may include the bayonet guide slots 111 spaced around a piston rod 180, which defines an axis 181 of the pump module 100 (FIGS. 1, 2a and 3a), and the reservoir module 200 may include the connecting structure 210, which comprises the guide pins 211 (FIG. 3b) and the opening 212 surrounding an axis 213 of the reservoir module 200 (FIGS. 1, 2a, 3b, 4b and 9). To connect the bayonet connector, the two modules 100 and 200 may first be aligned so that the openings are across from each other and the axes 181, 213 coincide, thus forming a common axis "C" (FIG. 1), e.g., a common axis of rotation for connection, and so that the guide pins 211 can be pushed into the guide slots 111. Then the two modules 100 and 200 are pushed together until the guide pins 211 reach the corners 111 a of the guide slots 111 (FIG. 3a). In a last step, the two modules are rotated relative to each other, so that the guide pins 211 are moved in the guide slots 111 in the direction of the ends 111 b of the guide slots 111. At the end of the movement (FIG. 2c), the two modules 100 and 200 may be locked together via a locking pin 142 (FIG. 3a) and the locking recess 242 (FIG. 3b), and the bottom plate of the housing 140 of the pump module 100 may lie parallel or coplanar to the bottom plate 241 of the reservoir module 200 extending from the housing 240 of the reservoir module 200 (FIG. 4b).

The rotation of the modules 100 and 200 relative to each other may be combined with a slight axial movement, where the two modules 100 and 200 may be drawn together, for instance in order to achieve a solid, low-play and low-tolerance seating of the reservoir module 200 on the pump module 100. The bayonet connector, as already noted, may provide for improved tolerances, and through the firm seating of the reservoir module 200 on the pump module 100, a transmission of forces, such as forces generated by the drive, between the modules may become unproblematic.

The administration device 1 may include a conventional delivery mechanism. To deliver medicament, the piston rod 180 may be disposed in the pump module and may be moved into reservoir 280 of the reservoir module 200 (FIG. 9). The piston 281 of the reservoir 280 may then be displaced and thus reduce the volume in reservoir 280, due to which medicament may be forced from the reservoir 280 and may be administered through the infusion path 290 and the infusion cannula 291 (see FIGS. 2a, 5c, and 9). The infusion cannula 291 may have been introduced into the tissue of the user by means of an insertion cannula 292 and an insertion mechanism 260 that may be connected to the infusion path 290.

Pump module 100 and reservoir module 200 may be connected to each other not only mechanically but also electrically when the bayonet connector is assembled. This may occur via the electrical contact arrangement 120 of the pump module 100 and the complementary electrical contact arrangement 220 of the reservoir module 200. According to the present disclosure, the electrical contact arrangements 120 and 220 may be geometrically set apart or displaced from the connecting structures so that, during the described rotation in the assembly of the bayonet connector, the relative path that the electrical contact arrangements 120 and 220 travel is greater than the path that, for example, the guide pins 211 travel. The electrical contact arrangement 120 of the pump module 100 may include a plurality of electrical contacts 121, which may be arranged in a strip or row on a plug 122 (FIG. 3a). Complementary to this, the electrical contact arrangement 220 of the reservoir module 200 may include a socket 222, in which the contact elements 221 may be arranged (FIGS. 3b, 4a and 4b). At the edge of the socket 222 there may be provided a sealing lip 223, which, when the bayonet connector is assembled, may serve to keep liquid from penetrating through the electrical contact arrangement into the reservoir module 200. The contact elements 221 may be configured to be elastic (e.g., spring-like), for example made of a metal press-bent part. In the assembly of the bayonet connector, the plug 122 may be pushed into the socket 222 and the contact elements 221 may contact the strip-shaped electrical contacts 121 on the plug 122. The strip shape of the electrical contacts 121 may enable contacting by the contact elements 221 along a certain path. The elastic design of the contact elements 221 may also enable the contact elements 221 to accept the axial movement superimposed on the rotation of the pump module 100 relative to the reservoir module 200 and may compensate for such movement during contacting.

The reservoir module 200 may include, as shown in FIGS. 4a, 4b, 5a, 5b, 5c, and 9, other elements in addition to those already mentioned.

Thus, the reservoir module 200 in one configuration may include at least one energy source, for example in the form of the primary cell or battery 230. The battery 230 may serve to supply electric energy to a secondary cell (for example, a rechargeable cell) disposed in the pump module and/or to the drive of the administration device 1. Further, the battery may be used to provide electrical and/or electronic elements that are disposed in reservoir module 200 with power. FIGS. 5a-5c show an example of how the battery 230 may be disposed in the reservoir module 200. In this embodiment, the battery 230 may be held in reservoir module 200 by a an electrical contact or battery contact 225, which may be configured as an extension or may have a reed shape. The battery contact 225 may be configured to be elastic like the contact elements 221, and may for example be made of a metal press-bent part. The battery contact 225 may contact one pole of the battery 230 and another contact may complete the electrical connection with the other pole of the battery 230.

Furthermore, the reservoir module 200 in one embodiment may include at least one circuit board 250 (FIGS. 5a to 5c). The circuit board 250 may include an electronic memory for storage of information. Data such as the date of manufacture of the reservoir module 200, serial number, data from sensors that may be present in the reservoir module 200, in particular a temperature log file, or operating parameters may be stored therein. Such types of data are non-exhaustive examples and it will be appreciated that other data may be stored in the electronic memory. Furthermore, the circuit board 250 may include circuitry for a control for the insertion mechanism 260 provided herein (FIG. 9). In some implementations, a release arrangement 270 for the insertion mechanism 260 may be controlled by the control (FIG. 9). The circuit board 250 may, for example, be connected to the battery 230 or the electrical contact arrangement 220 via the contacts 224 (for example in FIG. 5b). In some implementations, the contact elements 221, the contacts 224, and the battery contact 225 may be made of a press-bent metal-plastic hybrid component, such as of a component including a metal press-bent part spray-coated with an electrically insulating plastic. This may enable the press-bent plastic hybrid component to be installed on the reservoir module 200 with the battery 230 in a single assembly step, such as by being snapped on (see for example lock connection 226 in FIGS. 5a and 5b).

Further, in implementations, the reservoir module 200 may include the previously described release arrangement 270 for the insertion mechanism 260, and configurations of the arrangement 270 and the mechanism 260 are described in European patent applications 18199475.7, 17209749.5, 17209764.4, and 17209772.7, which are hereby incorporated by reference herein in their entirety for any purpose.

FIGS. 6 and 7 show a second embodiment according to implementations of the present disclosure. FIGS. 8a and 8b show two possible design details of the electrical contact pins 121' of the second embodiment. Differences from the first embodiment are discussed as follows. Other aspects largely correspond with the first embodiment and are incorporated in this embodiment by reference. The primary difference from the first embodiment lies in the electrical contact arrangements of pump module 100' and the matching or complementary reservoir module electrical contact arrangement. The electrical contact arrangement 120' may not include a single plug on which contacts are disposed, but may instead or additionally include individual electrical contact pins 121'. The reservoir module may include, in a complementary fashion thereto, individual sockets, e.g., parallel arranged sockets, for each contact pin of the electrical contact pins 121', e.g., parallel arranged pins. For instance, the individual sockets may be positioned floating in the reservoir module, and may compensate for axial motion during the rotational motion during the assembly of the bayonet connection. In an alternative configuration, the reservoir module for the second embodiment may be configured to be similar or even the same as in the first embodiment, and for instance only one socket may receive all electrical contact pins 121'. In this case, the contact elements in the electrical contact arrangement of the reservoir module may be geometrically shaped so they properly match the pins.

FIGS. 8a and 8b show two alternative designs of the contact pins. In FIG. 8a, each of the electrical contact pins 121' has a fixed length. FIG. 8b shows an alternative in which the pins are configured as spring-loaded and telescoping electrical contact pins 121", for example like "pogo sticks." Use of this alternative design of the telescoping electrical contact pins 121" may facilitate simplifying the electrical contact arrangement in the reservoir module. The electrical contact arrangement of the reservoir module may then have contact surfaces that are arranged more simply and unmovably on the reservoir module.

From the foregoing it will be appreciated that, although specific embodiments of the invention have been described herein for purposes of illustration, various modifications may be made without deviating from the spirit and scope of the invention. Accordingly, the invention is not limited except as by the appended claims.

REFERENCE NUMBER LIST

1 Administration device
100 Pump module
100' Pump module
110 Connecting structure, pump module
111 Guide slots, bayonet
111a Corners
111b End of guide slot
120 Electrical contact arrangement, pump module
120' Electrical contact arrangement, pump module
121 Electrical contacts
121' Electrical contact pins
121" Telescoping electrical contact pins
122 Plug
140 Housing, pump module
142 Locking pin
180 Piston rod, pump module
200 Reservoir module
210 Connecting structure, reservoir module
211 Guide pins, bayonet
212 Opening
220 Electrical contact arrangement, reservoir module
221, 221' Electrical contact elements
222 Socket
223 Sealing lip
224 Contact, circuit board
225 Battery contact
226 Lock connection
230 Primary cell or battery
240 Housing, reservoir module
241 Bottom plate, reservoir module
242 Lock connection recess
250 Circuit board, reservoir module
260 Insertion mechanism for infusion cannula
270 Release arrangement for insertion mechanism
280 Reservoir
281 Reservoir piston or stopper
290 Infusion path
291 Infusion cannula
292 Insertion cannula/needle

What is claimed is:

1. A modular administration device configured to be affixed to skin of a user, comprising
    a reservoir module comprising a reservoir, a reservoir module housing, a first connecting structure, and a first electrical contact arrangement, wherein the reservoir defines a first axis; and
    a pump module comprising a piston rod, a pump module housing, a second connecting structure disposed around the piston rod, and a second electrical contact arrangement, wherein the piston rod defines a second axis,
    wherein the first electrical contact arrangement is generally perpendicular to the first axis and the second electrical contact arrangement is generally perpendicular to the second axis,
    wherein the reservoir module and the pump module are releasably connectable via the first and the second connecting structures such that upon establishing a releasable connection, the piston rod is configured to cause a fluid medicament to be dispensed from the reservoir by a movement of the piston rod,
    wherein, to connect the reservoir module and the pump module,
    in a first step, the first and the second connecting structures are plugged together such that the first and second axes come to coincide and form a common axis of rotation, and
    in a second step, the pump module housing is rotated relative to the reservoir module housing about the common axis of rotation and the first electrical contact arrangement becomes electrically connected to the second electrical contact arrangement through such rotation,
    wherein the first electrical contact arrangement is positioned farther from the first axis in a radial direction than the first connecting structure, and the second electrical contact arrangement is positioned farther from the second axis in a radial direction than the second connecting structure.

2. The modular administration device of claim 1, wherein the first connecting structure and the second connecting structure together form a bayonet connector.

3. The modular administration device of claim 1, wherein the first electrical contact arrangement comprises at least one socket and the second electrical contact arrangement comprises at least one pin or plug that fits into the at least one socket in a complementary fashion.

4. The modular administration device of claim 1, wherein the first electrical contact arrangement comprises a plurality of parallel arranged sockets and the second electrical contact arrangement comprises a corresponding number of pins or plugs configured to fit into the plurality of parallel arranged sockets.

5. The modular administration device of claim 4, wherein axes of the plurality of parallel arranged sockets and the corresponding number of pins or plugs are generally perpendicular to the first axis or the second axis, respectively.

6. The modular administration device of claim 1, wherein the first electrical contact arrangement is mounted movably on the reservoir module housing.

7. The modular administration device of claim 6, wherein the first electrical contact arrangement is mounted such that the first electrical contact arrangement is floating on or in the reservoir module and is movable relative to the reservoir module housing.

8. The modular administration device of claim 6, wherein the second electrical contact arrangement is rigidly disposed on the pump module housing.

9. The modular administration device of claim 1, wherein the reservoir module further comprises a fluid pathway comprising an infusion cannula and an insertion mechanism for introduction of the infusion cannula into tissue of the user.

10. The modular administration device of claim 1, wherein the reservoir module further comprises an energy store for storing electrical energy and an electrical contact for such store.

11. The modular administration device of claim 10, wherein the energy store comprises a primary cell or a battery.

12. A modular administration device configured to be affixed to skin of a user, comprising
- a reservoir module configured for accommodating a reservoir, and comprises a reservoir module housing, a first connecting structure and a first plurality of electrical contacts; wherein the reservoir defines a first axis; and
- a pump module comprising a piston rod, a pump module housing, a second connecting structure disposed around the piston rod and a second plurality of electrical contacts, wherein the piston rod defines a second axis,
- wherein the first plurality of electrical contacts is generally perpendicular to the first axis and the second plurality of electrical contacts is generally perpendicular to the second axis,
- wherein the reservoir module and the pump module are configured for releasable connection via the first connecting structure and the second connecting structure such that upon establishing the releasable connection, the piston rod is configured to cause a fluid medicament to be dispensed from the reservoir by a movement of the piston rod, and
- wherein the first plurality of electrical contacts and the second plurality of electrical contacts are geometrically displaced from the first connecting structure and the second connecting structure, respectively, and
- wherein, to connect the reservoir module and the pump module, the first and the second connecting structures are configured to be pushed together in a first step, such that the first and second axes come to coincide and form a common axis of rotation, and in a second step, the pump module housing is rotated relative to the reservoir module housing about the common axis of rotation and the first plurality of electrical contacts becomes electrically connected to the second plurality of electrical contacts through such rotation.

13. The modular administration device of claim 12, wherein the first connecting structure and the second connecting structure together form a bayonet connector.

14. The modular administration device of claim 12, wherein the first plurality of electrical contacts and the second plurality of electrical contacts come into contact following a pre-defined sequence.

15. The modular administration device of claim 12, wherein rotation about the common axis of rotation in the second step causes an axial movement that draws the reservoir module and the pump module together and causes a firm seating of the reservoir module with the pump module.

16. The modular administration device of claim 14, wherein a grounding connection is established between the first plurality of electrical contacts and the second plurality of electrical contacts.

* * * * *